(12) United States Patent
Rezac et al.

(10) Patent No.: US 10,458,922 B2
(45) Date of Patent: Oct. 29, 2019

(54) METHOD OF DETECTING DEFECTS OF A MOVING SHEET OF FLEXIBLE FIBROUS MATERIAL

(71) Applicant: PFNONWOVENS CZECH S.R.O., Znojmo (CZ)

(72) Inventors: Frantisek Rezac, Sedlesovice (CZ); Zbynek Kadlc, Slapanice u Brna (CZ); Michal Nemec, Kucharovice (CZ)

(73) Assignee: PFNONWOVENS CZECH S.R.O., Znojmo (CZ)

( * ) Notice: Subject to any disclaimer, the term of this patent is extended or adjusted under 35 U.S.C. 154(b) by 0 days.

(21) Appl. No.: 15/743,001

(22) PCT Filed: Jul. 8, 2016

(86) PCT No.: PCT/CZ2016/000076
§ 371 (c)(1),
(2) Date: Jan. 9, 2018

(87) PCT Pub. No.: WO2017/008771
PCT Pub. Date: Jan. 19, 2017

(65) Prior Publication Data
US 2019/0086339 A1    Mar. 21, 2019

(30) Foreign Application Priority Data
Jul. 10, 2015   (CZ) .................................. 2015-488

(51) Int. Cl.
*G01N 21/00*    (2006.01)
*G01N 21/89*    (2006.01)
*G01N 21/88*    (2006.01)

(52) U.S. Cl.
CPC ..... *G01N 21/8915* (2013.01); *G01N 21/8851* (2013.01); *G01N 2021/888* (2013.01);
(Continued)

(58) Field of Classification Search
CPC ........... G01N 2021/8861; G01N 21/89; G01N 21/8917; G01N 21/8851; G01N 21/8915;
(Continued)

(56) References Cited

U.S. PATENT DOCUMENTS

| | | | | |
|---|---|---|---|---|
| 4,692,799 A | * | 9/1987 | Saitoh | .................... G01N 21/94 |
| | | | | 226/45 |
| 4,839,943 A | * | 6/1989 | Leifeld | .................... B07C 5/34 |
| | | | | 19/80 R |

(Continued)

*Primary Examiner* — Hoa Q Pham
(74) *Attorney, Agent, or Firm* — Amster, Rothstein & Ebenstein LLP (57) ABSTRACT

A defect detection method on a moving sheet of pliable fibrous material. The primary detection array is used to scan the moving sheet of fibrous material in at least one primary detection area, which fibers, after falling onto the moving belt, enter after a time shorter than 15 minutes. The secondary detection array scans the sheet of fibrous material in at least one secondary detection area, which the fibers, after falling on the carrying belt, reach later than the primary detection area, whereupon the information about the identified defects is sent to the assessment system, where, on the basis of information about at least some defects identified by the primary detection array, an area of the sheet of fibrous material is determined for which an assessment of defects identified by the secondary detection array will be performed.

8 Claims, 3 Drawing Sheets

(52) U.S. Cl.
CPC ............... *G01N 2021/8861* (2013.01); *G01N 2021/8864* (2013.01); *G01N 2021/8867* (2013.01)

(58) Field of Classification Search
CPC .. G01N 21/8983; G01N 21/86; G01N 33/365; G01N 33/36; G01N 2021/8864; G01N 2021/8867; G01N 2021/888
USPC ................ 356/429–431, 238.1, 238.2, 73.1; 348/88, 125; 382/111, 149
See application file for complete search history.

(56) References Cited

U.S. PATENT DOCUMENTS

| | | | | |
|---|---|---|---|---|
| 5,315,367 A | * | 5/1994 | Salvador | ............. G01N 33/362 |
| | | | | 356/238.2 |
| 7,372,553 B2 | * | 5/2008 | Aoshima | ................ G01M 11/37 |
| | | | | 356/73.1 |
| 8,175,739 B2 | * | 5/2012 | Floeder | .................. G01N 21/89 |
| | | | | 700/122 |
| 2015/0085276 A1 | * | 3/2015 | Uchino | .................... D06H 1/02 |
| | | | | 356/73 |

* cited by examiner

| W2 mm (up to) | Roll number | Primary assessment ||||| Secondary assessment ||||
|---|---|---|---|---|---|---|---|---|---|---|
| | | Package 1 | Package 2 | Package 3 | Discarded | Verification | Package 1 | Package 2 | Package 3 | Discarded |
| 150 | 1 | | V14 | | 1 | | | ✗ | | 1 |
| 300 | 2 | | | | | | | | | |
| 450 | 3 | V8 | V10 | | 1 | 1 | ✗V81 | ■ | | 2 |
| 600 | 4 | | V10 | | | 1 | | | | |
| 750 | 5 | V5 | | | 1 | | | ✗ | | 1 |
| 900 | 6 | V4 | | | 1 | | | ✗ | | 1 |
| 1050 | 7 | V1 | V12 | | 2 | | | ✗ | | 2 |
| 1200 | 8 | | | | | | | | | |
| 1350 | 9 | | | | | | | | | |
| 1500 | 10 | | | | | | | | | |
| 1650 | 11 | | | | | | | | | |
| 1800 | 12 | | | | | | | | | |
| 1950 | 13 | | | | | | | | | |
| 2100 | 14 | | | | | | | | | |
| 2250 | 15 | V2 | | V16 | 1 | 1 | | ✗ | | 1 |
| 2400 | 16 | | V15 | V16,V17 | 1 | 1 | | ✗ | ■ | 2 |
| 2550 | 17 | | | V17 | | 1 | | | ■ | 1 |
| 2700 | 18 | | | | | | | | | |
| 2850 | 19 | | | | | | | | ■ | 1 |
| 3000 | 20 | | | | | | | | | |
| 3150 | 21 | | | | | | | | | |
| 3300 | 22 | V3 | V13 | | 1 | 1 | ✗ | ▨ | | 2 |
| 3450 | 23 | | V13,V9 | | | 1 | ✗ | ▨ | | 1 |
| 3600 | 24 | V7 | | | 1 | | ✗ | | | 1 |
| 3750 | 25 | | | V19,V20 | 1 | | | | ✗ | 1 |
| 3900 | 26 | V6 | | V18 | | 2 | | | ▨ | 1 |
| 4050 | 27 | V6 | V11 | V18 | | 3 | ■ | ▨ | ▨ | 3 |
| 4200 | 28 | | V11 | | | 1 | | ▨ | | 1 |
| Total | | | | | 24 | | | | | 22 |

FIG. 3

METHOD OF DETECTING DEFECTS OF A MOVING SHEET OF FLEXIBLE FIBROUS MATERIAL

CROSS-REFERENCE TO RELATED APPLICATIONS

This application is the United States National Phase of Patent Application No. PCT/CZ2016/000076 filed 8 Jul. 2016, which claims priority to Czech Republic Patent Application No. PV 2015-488 filed 10 Jul. 2015, each of which are incorporated herein by reference.

BACKGROUND OF THE INVENTION

Field of Art

The invention relates to a method for detecting defects on a moving sheet of pliable fibrous material, namely nonwoven textile, created by fibres falling onto a carrying belt, whilst a primary detection array scans the moving sheet of fibrous material in at least one primary detection area, which the fibres, after falling onto the carrying belt, enter after a time less than 15 minutes, better yet less than a minute and preferably less than 20 seconds, and information about the identified defects is sent for assessment, where it forms the basis for assessing the need to adjust production parameters.

The requirements on the homogeneity of produced fibrous materials, for example in the form of a nonwoven textiles, are continuously increasing. During the course of the production process, various types of local material inhomogeneities may form, which from a certain degree constitute a defect and are undesirable in subsequent processing. The requirements of individual converters differ based on the target application, meaning that an inhomogeneity that constitutes a critical defect for one converter may be acceptable for another converter. With respect to the increasing demands on production line output coupled with demands for a reduced basic weight of the material, the speed at which the textile travels through the production line continues to increase. It is known in the industry that there are inspection systems for moving materials based on various principles that monitor various types of local inhomogeneities. For the identification of defects visible with the human eye (and thus easily recognisable by the customer on the final product) optical systems working on, for example the principle described in patent application EP2221607 submitted by Voith and published 25 Aug. 2010 are used.

There are various types of commercial optical detection systems from various suppliers available on the market. It can generally be said that modern detection systems presently contain a combination of several measurements. For example, one method has the light source located on one side of the material with the detection camera located on the other side ("transmission"). The defect on the material shows up as a dark shadow or otherwise a light area relative to the surrounding area. Another method has the light source and the detection camera located on the same side of the material and the detection camera scans the reflected light ("reflection"). The defect or contamination manifests itself as a colour change relative to the surrounding area. Each of these methods is optimal for registering one of the different types of defects and by combining them in a single detection location it is possible to achieve the proper documentation of all defects.

Fibrous-type materials—such as for example nonwoven textiles—exhibit a certain degree of implicit inhomogeneity due to the inherent characteristics of the production process. As is known in the industry, an appropriate algorithm is essential for the correct determination of defects. The algorithm assesses the picture registered by the detection system and marks defects. The system can be either fully automatic or combined with an operator.

When assessing defects, the position of the monitoring station is also important. Normally, it is located directly after the formation of the textile. After passing through the monitoring station the material has a long journey to the final cutting and packaging processes. There are various defect marking systems known in the industry. For example U.S. Pat. No. 8,175,739 dated 8 May 2012 and application WO 2009/129082 submitted on 7 Apr. 2009 (both are from 3M Innovative Properties), which work on marking the defect location on a textile and subsequent detection. The described system makes it possible to even transport the material from one location to another and to subject it to various subsequent modifications without the loss of information about the location of the defect. A similar principle with another type of marking is described, for example, in patent application WO 2009/042638 submitted by Hellstrom on 24 Sep. 2008. The disadvantage of the known present state of technology is, in particular, the fact that it does not deal with identifying the location of the defect along the width of the material, meaning that for identified defects it is always necessary to reject the material in its entire width.

With growing production line outputs and reduction of material basis weights, the speed of production lines is rapidly increasing. For example, production lines using spunlaid technology are presently reaching speeds of over 1000 m/min, which in combination with a certain degree of inhomogeneity of the textile given by the production process and the declining thickness linked with a growing transparency of the material, presents a considerable challenge for online detection systems.

It could be reasonable to conclude that when nonwoven textile production speeds become comparable with those of paper production, then the solutions used in the paper making industry will be entirely suitable for defect detection. The present modem nonwoven textile is characterised, however, by several differences making a simple technology transfer impossible.

The demands, namely in the hygiene product industry, placed on the specifications of nonwoven textiles consist of specific properties based on the application, nevertheless, it generally applies that the overall basis weight is being reduced, requirements for softness are growing as are requirements for bulkiness of the material. This means that the textile is, in general, being produced using increasingly smaller amounts of material and to maintain opacity, the diameter of fibres is declining in at least one layer of the textile. At the same time it is necessary to retain the impression that the end customer is used to. It is desirable that the product produced from low basis weight materials, apart from having a reliable function, also gives the customer the impression of quality, reliability and it should provide a pleasant impression when touched. That is why modern materials take advantage of, for example, crimped fibres (e.g. Czech Patent Application No. 2013-024), various softening additives for smooth touch and feel and drapeablity (e.g. Czech Patent Application No. 2012-655) and materials are bonded with emboss patterns with specific shapes and arrangements of bonding points (e.g. WO 2011131156), which are also characterised by a smaller bonding surface area than standard embossing patterns.

From the above description, it is evident that a nonwoven textile differs from paper by, for example, the texture of its surface. Whereas paper is generally smooth and flat, a nonwoven textile is an irregular 3D fibrous structure with pronounced bonding points and variable material transparency.

Another difference is the pliable nature of these textiles. Under the effect of tensile forces on the production line, changes in the textile occur, resulting in a change in length (lengthening of the material), width (narrowing of the material) and basis weight (when the tensile force is released the material shrinks relative to its initial dimensions). The above-mentioned defect location marking systems mark the position of the defect on the length of the roll, they do not monitor the movement of the defect along the width, or they work with a stronger material where this problem does not arise. As a result, every identified critical defect means that the produced textile needs to be discarded or recycled or at least set aside for a less demanding application along the entire width of the sheet of material.

SUMMARY OF THE INVENTION

The principle of the invention is a method for detecting defects on a sheet of pliable fibrous material that is falling onto a carrying belt; where the primary detection array scans the moving sheet of fibrous material in at least one of the primary detection areas (A), which the fibres reach after falling onto the carrying belt within a time shorter than 15 minutes, preferably in less than a minute and better yet in a time less than 20 seconds, preferably in a time less than 10 seconds, and the information about the identified defects is sent for assessment on the basis of which, for example, the need for adjustment of production parameters is assessed, wherein the secondary detection array scans the sheet of fibrous material in at least one secondary detection area (B), which the fibres reach, after falling onto the carrying belt, later than the primary detection area (A), whereupon the information about the identified defects is sent to the assessment system, during which time, based on the information of at least certain defects identified by the primary detection array (A), it determines the area of the sheet of fibrous material, for which an assessment of the defects identified by the secondary detection array (B) will be performed, and this assessment is performed. For the solution according to the invention it is advantageous, when the expected measurement error of the defect's coordinates is defined and when the coordinates of the defects identified by the primary array are compared within the assessment system with the information about the expected cut lines in the subsequent cutting of the sheet of fibrous material into separate sheets and the defects identified as lying on the expected cut line or at a distance smaller or equal to double the expected measurement error from the expected cut line are paired with the respective defects identified by the secondary detection array and these defects are assigned coordinates identified by the second detection array, and the assessment of the defects identified by the secondary detection array is performed only for the areas corresponding to the expected separate sheets not containing defects the coordinates which were described by the process above or defects identified by the primary array as lying at a distance corresponding to at least double the expected measurement error.

Advantageous configurations of the invention are described in the dependent patent claims.

BRIEF DESCRIPTION OF THE DRAWINGS

The invention is further described using exemplary embodiments and references to attached drawings, where in FIG. 1A the online nonwoven textile production system enabling defect detection according to this invention is presented schematically.

General Method for Executing the Invention

Figure 1A:
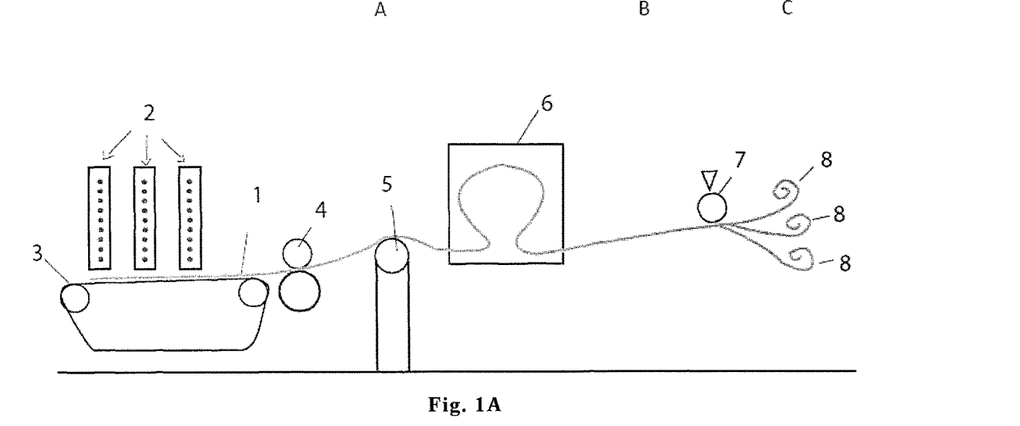
Figure 1B:
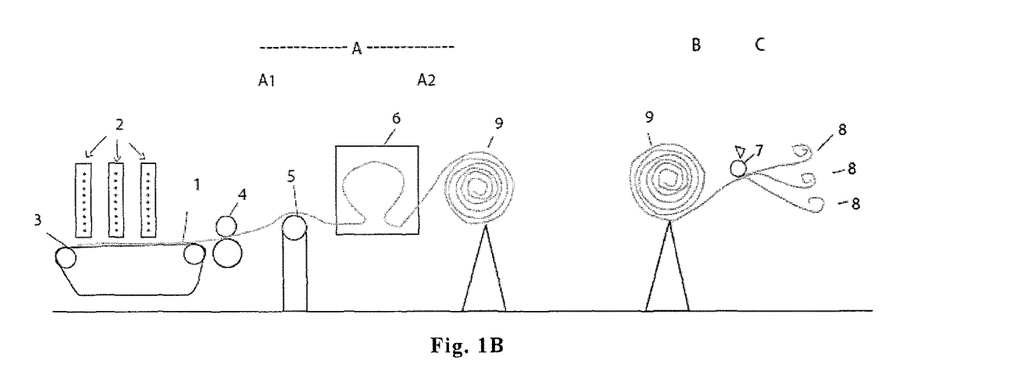
in FIG. 1B there is a similar illustration, however for an offline system.

As shown on FIG. 1, the production of nonwoven textiles 1 consists of formation from fibres created using, for example an array of spinnerets 2, for example by deposition on a moving belt 3. The created layer of fibres is subsequently bonded in a bonding mechanism 4 (e.g. thermally). Subsequently, it can be modified using various methods. Standard methods include for example, wet treatment in the wet treatment mechanism 5 followed by drying in the drying station 6. The finished nonwoven textile 1 either continues directly to the cutting station 7 and packing in the online system (FIG. 1A), or it is wound onto one "jumbo" roll 9 in the offline system (FIG. 1B). This roll is then moved to the cutting station 7, again unwound and the material is cut to size and wound onto rolls 8 according to the customer's requirements. It is normal for the cutting station 7 to be located directly behind the wound up jumbo roll 9.

The defect detection system is usually located in such a way that it scans the detection area $A_1$ directly after the textile is formed and strengthened before the first treatment (between the bonding mechanism 4 and the wet treatment mechanism 5). Such a location makes it possible to flexibly reconfigure production parameters e.g. in the event that the system starts detecting an increased number of defects. On the other hand, a disadvantage of this is the long path of the material after the detection station, where the material may be contaminated or new defects may form.

A second suitable primary detection area $A_2$ of the defect detection system is located directly before the winding of the material—in online systems this location is practically the same as the secondary detection area B, which is located closely before the cutting station 7. In offline systems the second primary detection area $A_2$ is usually located directly before the winding of the jumbo roll 9. This position also detects defects and contamination that arose during the treatment processes. Considering the usually small number of online treatments, the defect detection is still sufficiently fast for the flexible adjustment of production parameters.

It generally applies that the detection system marks every detected defect 13—either physically or using software (e.g. by recording the coordinates). When the zero point 0 ($L_0$, $W_0$) is known, it should then be simple to determine the position of the defect and when cutting the material into narrow rolls 8, a standard procedure, for example, in case of orders for hygiene industry, it should be possible to determine the narrow roll 8 in which the defect 13 is located (see FIG. 2A). Given the pliable nature that is typical namely for soft or thin nonwoven textiles, the tensile forces acting on it result in changes in the length and width of the nonwoven textile. Generally, for example, the length (MD direction) of the nonwoven textile may increase and the width (CD direction) of the nonwoven textile may decrease as it travels along the production line (FIG. 2B). In order to determine the precise position of the defect 13 on the narrow rolls 8, it is then necessary during the detection process, apart from the identified positions ($L_1$, $W_1$) of the defect 13, to consider the effect of the changes resulting from tensile forces and to recalculate the values to represent the actual position ($L_2$. $W_2$). On the one hand, the calculation helps to determine the position of the defect 13 on uncut narrow rolls 8, on the other hand it is necessary to include a certain degree of uncertainty and to present the location of the defect 13 with a probability interval. In the event that the location of the defect 13 lies close to the cut line, the probability interval then extends into the two adjacent narrow rolls 8. Given the uncertainty of the location, it is then necessary to discard both narrow rolls, which increases the amount of scrap.

A solution could be to locate the defect detection system directly before the cutting station 7 in position B. When the online system is used, no problems arise, in the case of the offline system it is necessary to consider the elapsed time after which the material 1 reaches the cutting station 7, which is generally in the range from several minutes to several hours, but a situation may arise where the material reaches the cutter only after several days. This type of system thus loses the option of flexible adjustments to the configuration of the production line based on the detection of typical defects. For example, during spunmelt production a situation may occur where recurrent small drips are formed, which at the applied production speeds are very difficult to spot with the human eye. If the recurring dripping defect is not detected immediately by the detection system and the process parameters are not adjusted, it is possible that large amounts of produced material may need to be scrapped.

The principle of the invention is in the combination of several detection locations on the production line. The primary detection location is located in position A, sufficiently close after the formation of the textile so as to enable the flexible reaction of producer to the detected defect. The time from when the fibres fall onto the carrying belt to the time the defects are detected should be less than 15 minutes, preferably less than a minute, better yet less than 20 seconds, preferably less than 10 seconds.

It is advantageous to position the primary detection area $A_1$, directly behind the location where the textile is formed and strengthened. The advantage of this position is the immediate detection of defects from the formation of the textile, thus enabling a flexible reaction in the configuration of production parameters. At the same time, none of the defects are masked in the subsequent processes by the used treatments.

In offline systems it is advantageous to locate the primary detection position $A_2$, directly before the winding mechanism 9, that is, at the end of the first uninterrupted part of the process. The advantage of this position is that reaction flexibility is maintained, while the detection of defects not only from the formation of the textile but also from the treatments performed before the detection location is possible. A person skilled in the characteristics of textile production and subsequent treatments is easily able to determine, which position is the most appropriate with respect to the characteristics of textile formation and the subsequently used treatments.

The primary detection system in the primary detection location scans the moving textile at its production speed, and based on the configured parameters detects defects. Each defect is marked using a unique identifier (for example a sequence number) and its position is determined from the zero point ($L_0$; $W_0$) by coordinates determining the longitudinal distance $L_1$ and the transversal distance $W_1$. The system is also able to store additional information about every defect, such as for example the size of the detected defect, the assumed defect type assessed by an algorithm. One of the possible principles is described in, for example, U.S. Pat. No. 8,175,739 granted on 8 May 2012 to 3M Innovative Properties.

The primary detection system may consist of a single detection station or several detection stations in various locations of position A. For example, one primary detection location may be located downstream the calender, i.e. the bonding mechanism 4, the second primary detection location downstream the wet treatment mechanism 5 and a third primary detection location downstream the dryer 6. For the invention it is significant, that the primary detection location is located sufficiently close after the formation of the textile to enable a flexible changes in production and at the same time it is assessed as a primary detection location, as described below.

The secondary detection location is located in position B, advantageously directly upstream the cutting station 7, preferably directly before the location where the blade cuts the textile. The secondary detection system in the secondary detection location scans the moving textile at its speed, and based on the configured parameters detects defects. Each defect is marked using a unique identifier (for example a sequence number) and its position is determined from the zero point 0 ($W_0$; $L_0$) by coordinates determining the longitudinal distance $L_2$ and the transversal distance $W_2$. Given the pliable nature of the textile and thus namely the length and width of the moving textile sheet, the values $L_1$ and $L_2$, as well as $W_1$ and $W_2$ may differ significantly. It is not possible to automatically assume that by simply assigning defect sequence numbers from the primary to those from the secondary detection location, the defects will be paired.

It could be assumed that if we measure the width of the nonwoven textile in the primary detection location A and at the level of the cutting blades at the cutting station 7, we will collect a sufficient amount of information for a simple recalculation of the defect location position—a so-called stretch coefficient. Reality has shown, that namely for nonwoven textiles with a higher degree of compliance, this simple connection does not apply. One factor is the actual measurement of the width of the nonwoven textile sheet, which due to the effect of the irregularity of its edges fluctuates and only an approximate average can be inferred. Another factor is the variability of the characteristic of the textile depending on ambient conditions. For example, the changing ambient temperature over the course of the day may affect the degree of compliance. Or for example the changing friction on the surface of the roller (e.g. when undesirable deposits form) causes a change in the resistance created by the roller and as such may cause a change in the stretching of the textile. In intermittent measurements it is thus necessary to expect further errors caused by various factors.

The secondary detection location provides several advantages. For example, as mentioned above, it detects new defects and contaminations, which arose after the primary detection location. For example, it also serves to specify more precisely the position of the defect detected by the primary detection system. Finally, it also has a backup function and in the event that the primary detection location goes out of operation, it inspects the textile and the detection of all arisen defects.

The secondary detection location in position B configured to the same settings generally detects the same or a larger number of defects as the primary detection location in position A. This, however, must not necessarily apply if the conditions at the detection stations are different. For example, if the material movement speed is not the same or if a production step is performed between the stations, which could mask the defects.

Assessment can be approached in several ways.

For example, it is possible to separately assess the defects on the primary detection location for the needs of configuring production parameters and separately assess the defects from the secondary detection location for the needs of quality control of materials and the detection of defects so that they are not sent to the customer. In this case, the assessment is performed twice, entirely independently and the results are not compared in any way. In the event of an assessment error at the second station, a verification with the first station is not performed, and furthermore a part of the work is performed twice.

For example, it is possible to assign every defect 13 detected by the primary detection array its detection by the secondary detection array. The assessment of data from the secondary detection array then consists in improving the precision of the position of the detected defects 13 and the assessment of unpaired—that is undetected or newly arisen defects 13. This assessment method provides perfect information about the positions of individual defects 13 and changes in the sheet of material that occur between the detection areas. On the other hand it places considerable demands on computing technology during automatic pairing or human resources during manual pairing.

Figure 2A:
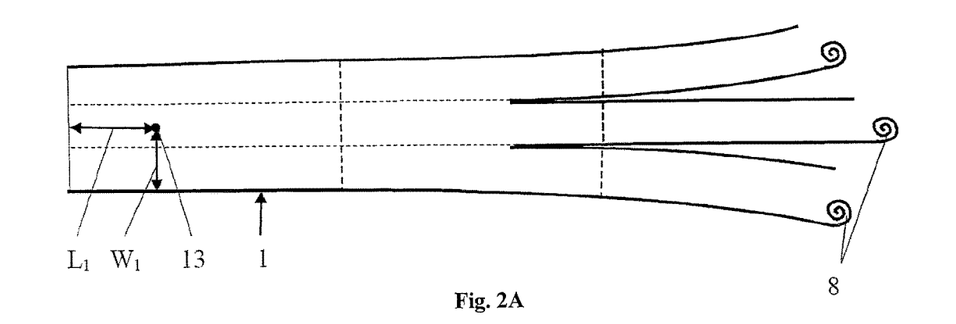
in FIG. 2A there is a schematically presented view of the already partially cut inspected textile with marked expected cut lines.
Figure 2B:
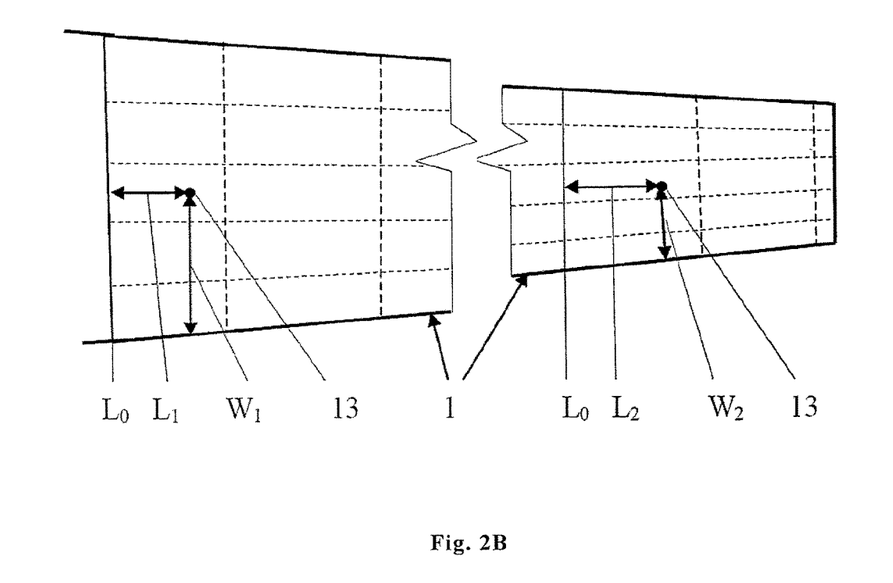
in FIG. 2B there is a schematically presented view of the inspected textile with the expected cut lines marked out and with shape changes.

It is also advantageous to assess defects 13 detected by the primary detection array and to project them onto a grid consisting of the projection of the cuts into the surface of the textile sheet (FIG. 2A, 2B). Given the variable dimensions of the textile sheet it is possible to use a rough conversion calculation of the position of the cut and the position of the defects according to the average characteristics of the material. A calculation error is subsequently taken into account by determining a safe distance of the defect 13 from the future cut location. It is then possible to mark the future narrow rolls 8, where the critical defect 13 is located at a safe distance from the cut and not assess these areas in the data from the second detection array. At the same time it is possible to mark critical defects 13, which are located too close to the future cut and to pair these with their detection by the second detection array and to improve the precision of their positions (in particular with respect to determining the final narrow roll 8 where they will be located). Areas not rejected by the first detection array can be assessed as newly arisen defects 13.

The safe distance of a defect 13 from the future cut is generally dependent on multiple parameters during the course of the processes. For example, during offline cutting, illustrated in FIG. 1B, the essential factors are the precision with which the textile is guided and also the precision with which the jumbo roll 9 is seated on the cutter—the textile sheet must not be subject to unregistered movement relative to the coordinates. From the physical standpoint however, every measurement and process cannot be performed with absolute precision but with a certain deviation. If the measurement and process step deviations are known, it is possible to calculate the deviation of the position of the defect 13 on the blades both in the MD ($L_2$), as well as the CD ($W_2$) direction. A well known rule can be used for this calculation:

If it is true that a physical value X, which needs to be determined, is a function of physical values a, b, c, . . . contained in a given formula, i.e.

$$X = f(a,b,c,\ldots)$$

We designate the probable errors of values a, b, c . . . as da, db, dc. The sought probable error of value X will be designated as dX. Its calculation can be performed using equation $$dX = \text{square root}((\delta f/\delta a * da)^2 + (\delta f/\delta b * db)^2 + (\delta f/\delta c * dc)^2 + \ldots)$$

where partial derivatives of function f (a, b, c . . . ) come out gradually based on the variables a, b, c.

The individual values may be, for example, the measuring accuracy of the nonwoven textile sheet (+−x mm in the CD direction), the accuracy with which the jumbo roll is seated before the cutter (shifting of zero in the coordinates +−x mm in the CD direction), the measuring accuracy of the length of the nonwoven textile sheet (+−x mm in the MD direction), the accuracy of determining the position of the defect by the detection system (+−x mm in the CD and MD direction) etc. An example of a calculation is provided in example 0. Depending on the quality control policy, it is then possible to set a multiple of the error value, which will be considered to represent a safe distance. For example, it may be just the calculated deviation, better yet a multiple of one and a half, and preferably double the calculated deviation. For example, for spunmelt-type material in offline cutting at a reasonable precision of operations, a safe distance may constitute 10 mm from the location of the cut, better yet 15 mm and preferably 20 mm. A person skilled in the art can, based on knowledge of the process and the above described calculation, easily determine the safe distance from the location of the cut for a given production process.

With advantage it is possible to add a tertiary detection array to the two detection location system. This detection system scans a tertiary detection area C arranged behind the location of the cut at the cutting station 7 before the winding onto the narrow rolls 8. The main objective when using the tertiary detection array is no longer the detection of defects assessed by the preceding stations, but an inspection of the cut of the nonwoven textile. The cameras of the tertiary detection array can, for example be pointed at the surface of the roller, which transfers the textile from the cutting location and against which the textile has good discernibility. As a result of tension in the textile; from the location of the cut, the cut opens up and stripes of textiles interchanging with stripes of the roller are discernible. By scanning and assessing the picture of the roller, we can assess, for example, the regularity of the cut on the textile and record especially cutting defects related to, for example, tearing of the textile on the blade or possibly a defect exhibited by an imperfect cut.

The described method of assessment of defects on the textile can be used on a wide range of materials under a wide range of conditions.

It is advantageous to use it especially for materials with a basis weight of 150-5 g/m², better yet 70-5 g/m², better yet 50-5 g/m², and preferably 30-5 g/m².

It is advantageous to use it especially at operating speeds of 10-1500 m/min, better yet 100-1500 m/min, better yet 250-1200 m/min, and preferably 500-1200 m/min.

It is advantageous to use it for a textile, better yet for a nonwoven textile and preferably for a spunmelt-type nonwoven textile, which can consist of several layers of fibres. The layers of fibres can, in essence, be the same (for example spunbond-spunbond-spunbond=SSS material), or they can differ by the characteristic of the fibres, whether in terms of the fibre thickness (for example spunbond-spunbond-meltblown-spunbond=SSMS material or SMS, SSM- MMMS, etc.) or by the composition of the fibres (the additivation of one of the layers). A person skilled in the art can easily identify many other possibilities.

Advantageously it is possible to use the method for a textile made primarily from polyolefins, better yet from polypropylene, polyethylene, copolymers or a combination thereof. Likewise, also for textiles containing significant amount of, for example, aliphatic polyesters (e.g. polylactic acid—PLA) or, for example other biopolymers or, for example, elastomers of various types. For the application of the advantages of the defect detection method according to the invention, the characteristic of the input polymer itself is not significant, but rather the final characteristic of the produced nonwoven textile. A person skilled in the art can easily estimate by trial, whether the textile from specific polymers will be rigid and whether it will remain spatially stable when moving along a specific production line and whether compliance of the textile will be exhibited and whether changes in the shape of the textile sheet will occur.

The advantages of the procedure according to the invention will be evident in a production process, where the width of the textile in the location of the cut with the blade in the cutting station 7 makes up less than 100%, namely less than 98%, better yet less than 96%, of even less than 95% of the width of the textile sheet in the location directly after bonding in the bonding mechanism 4.

The described method for using the primary and secondary detection system and the assessment of defects on the textile brings several advantages.

For example it is possible to turn over the jumbo roll between the primary detection area A and the secondary detection area B so that then the primary detection array scans defects on the textile from one side (for example, from the smooth side) and the secondary detection array scans the textile from the second side (for example, from the side with the emboss pattern).

For example, it is also possible to temporarily use the detection arrays as a mutual backup and when an outage or defect occurs on one of the detection arrays, use only the data from the second detection array for discarding rolls after cutting. Indeed, not all the advantages of the invention will be exploited in that case, however for a limited time the system may be kept in operation.

An advantageous configuration according to the invention can be, for example, the detection of defects 13 in a nonwoven textile the width of which at the location of the cut with the blade in the cutting station 7 accounts for less than 100%, possibly less than 98%, better yet less than 96%, and preferably less than 95% of the width of the textile sheet in the location directly after the bonding in the bonding mechanism 4, moving at an operating speed of 10-1500 m/min, better yet 100-1500 m/min, better yet 250-1200 m/min, and preferably 500-1200 m/min, having a basis weight of 150-5 g/m2, better yet 70-5 g/m2, better yet 50-5 g/m2, preferably 30-5 g/m2.

For detection, for example, a combination of one primary and one secondary detection array is used. The primary detection array scans the moving sheet of fibrous material in at least one primary detection area (A), which the fibres, after falling onto the carrying belt, enter after a time less than 15 minutes, better yet less than a minute, better yet less than 20 seconds, preferably less than 10 seconds, and information about the identified defects is sent for assessment, where it forms the basis for assessing the need to adjust production parameters.

The secondary detection array scans the sheet of fibrous material in at least one secondary detection area (B), which the fibres, after falling on the carrying belt, reach later than the primary detection area (A), whereupon the information about the identified defects is sent to the assessment system, where, on the basis of information about at least some defects identified by the primary detection array (A), an area of the sheet of fibrous material is determined for which an assessment of defects identified by the secondary detection array (B) will be performed, and this assessment will be performed.

For example, it is possible to assess defects detected by the primary detection position and to project them into a grid consisting of the projection of the cuts into the surface of the textile sheet (FIG. 2A, 2B). Given the variable dimensions of the textile sheet it is possible to use a rough conversion calculation of the position of the cut and the position of the defects according to the average characteristics of the material. A calculation error is subsequently accounted for by determining the safe distances of the position of the defect from the future cut area, which can be, for example, one and a half times the calculated calculation error. It is then possible to mark the future rolls, where the critical defect is located at a safe distance from the cut and not assess these areas at the second position of the cameras. At the same time, it is possible to mark critical defects which are located too close to the future cut and to pair these with their detection by the second detection location and to improve the precision of their positions (in particular with respect to determining the final roll 8 where they will be located). Areas not rejected by the first detection location can be assessed as newly arisen defects.

EXAMPLES

Example 0—Comparative Example

On spunbond-type nonwoven textile made from polypropylene, the primary detection area A1 is arranged directly upstream the winding onto a jumbo roll 9. The material is then transferred to the cutting station, where it is unwound and cut into 150 mm wide rolls.

A simple conversion calculation is used to identify the position of the defect at the cutting station 7

$$W_2 = K * W_1$$

Where the coefficient K is defined from the width of the textile sheet in the detection area A1 and the width of the textile sheet in area $A_2$ at the cutting station. $K = A_2/A_1$.

The dimensions $A_1$ and $A_2$ are set with a deviation of +−10 mm.

The deviation of coefficient K is thus set according to the calculation:

$$dK = \text{square root}((1/A_1 * 1 * 10)^2 + (A_2 * ((-1)/A^2) * 10)^2)$$

Distance $W_1$ is set with a deviation of +−5 mm.

The deviation of distance $W_2$ is thus set according to the calculation:

$$dL_2 = \text{square root}((W_1 * dK)^2 + (K * dW_1)^2) = 0.23\%$$

The error caused by the imprecise attachment of the jumbo roll before unwinding or the imprecise guiding of the textile is ignored. The table shows deviations for recalculated defects for specific cases:

| Sample | A-0 | B-0 | C-0 | D-0 |
|---|---|---|---|---|
| Type of emboss pattern: | G1 | G2 | G2 | G2 |
| surface treatment of material | no | no | no | hydrophilic |

-continued

| Sample | A-0 | B-0 | C-0 | D-0 |
|---|---|---|---|---|
| basis weight (g/m2) | 15 | 17 | 18 | 18 |
| width of the material in the bonding mechanism 4 (mm): | 4464.3 | 4454.2 | 4460.0 | 4461.4 |
| width of the material in detection area $A_1$ (mm): | 4371.4 | 4241.7 | 4240.0 | 4194.3 |
| width of the material at the cutting station 7 (mm): | 4327.1 | 4135.8 | 4150.0 | 4022.9 |
| width of the textile at the cutting station 7 relative to its width at the bonding mechanism 4 (%): | 96.9% | 92.9% | 93.0% | 90.2% |
| width of the textile at the cutting station 7 relative to its width at the detection area A1 (%): | 99.0% | 97.5% | 97.9% | 95.9% |
| deviation of the position of the defect after recalculation (± mm): | 9.8 | 9.5 | 9.5 | 9.4 |

Therefore, for the defects found on the cut closer than the value in the last row of the table, there is a significant probability of the position of the defect on both sides of the cut and it is thus necessary to discard both adjacent rolls.

Example 1—Pairing of Individual Defects

On a spunbond-type nonwoven textile made from polypropylene, the primary detection area $A_1$ is arranged directly upstream the winding onto a jumbo roll. The secondary detection area B is directly upstream the location of the cut of the textile at the cutting station 7. It is cut into rolls with a width of 150 mm.

The distance $W_1$ and $W_2$ are set with a deviation of +−5 mm.

The individual defects detected at the primary detection location A1 are paired with the defects detected in the secondary detection location B. The secondary detection location B detected 2 more defects. The deviation for determining the position of the secondary detection location is +−5 mm. The same deviation applies in the location of the cut.

Therefore, for the defects found closer than 5 mm, there is a significant probability of the position of the defect on both sides of the cut and it is thus necessary to discard both adjacent rolls.

| Sample | A-1 | B-1 | C-1 | D-1 |
|---|---|---|---|---|
| Type of emboss pattern: | G1 | G2 | G2 | G2 |
| surface treatment of material | no | no | no | hydrophilic |
| basis weight (g/m2) | 15 | 17 | 18 | 18 |
| width of the material in the bonding mechanism 4 (mm): | 4464.3 | 4454.2 | 4460.0 | 4461.4 |
| width of the material in detection area A1 (mm): | 4371.4 | 4241.7 | 4240.0 | 4194.3 |
| width of the material at the cutting station 7 (mm): | 4327.1 | 4135.8 | 4150.0 | 4022.9 |
| width of the textile at the cutting station 7 relative to its width at the bonding mechanism 4 (%): | 96.9% | 92.9% | 93.0% | 90.2% |
| width of the textile at the cutting station 7 relative to its width at the detection area A1 (%): | 99.0% | 97.5% | 97.9% | 95.9% |
| deviation of the position of the defect after recalculation (± mm): | 5.0 | 5.0 | 5.0 | 5.0 |

In the case of the specific assessment of the material according to example zero and one, sheet of material A was considered, which was subsequently divided into rolls with a width of 150 mm and a random distribution of drips along the width. The calculated deviation of the position of the defect was multiplied by the safety coefficient and if it encroached into the area of the possible presence of a defect on two adjacent rolls, then both adjacent rolls were marked to be discarded.

| Sample | A |
|---|---|
| Type of emboss pattern: | G1 |
| surface treatment of material | no |
| basis weight (g/m2) | 15 |
| width of the material in the bonding mechanism 4 (mm): | 4464.3 |
| width of the material in detection area A1 (mm): | 4371.4 |
| width of the material at the cutting station 7 (mm): | 4327.1 |
| width of the textile at the cutting station 7 relative to its width at the bonding mechanism 4 (%): | 97% |
| width of the textile at the cutting station 7 relative to its width at the primary detection area A1 (%): | 99% |
| deviation of the position of the defect after recalculation (± mm): | 9.8 |
| Deviation of the position of the defect when detected in detection area A2 (± mm) | 5.0 |
| safety coefficient | 2 |
| width of the roll (mm) | 150 |

| Defect number | A-0 (detection in A area only) | | | | A-1 (detection also in B area) | | | |
|---|---|---|---|---|---|---|---|---|
| | W1 | W2 min | W2 max | discarded rolls | W2 | W2 min | W2 max | discarded rolls |
| V1 | 274 | 252 | 291 | 1 | 271 | 261 | 281 | 1 |
| V2 | 503 | 478 | 517 | 1 | 498 | 488 | 508 | 1 |
| V3 | 591 | 566 | 605 | 2 | 586 | 576 | 596 | 1 |
| V4 | 879 | 851 | 890 | 1 | 870 | 860 | 880 | 1 |
| V5 | 1023 | 993 | 1033 | 1 | 1013 | 1003 | 1023 | 1 |
| V6 | 1090 | 1060 | 1099 | 1 | 1079 | 1069 | 1089 | 1 |
| V7 | 1122 | 1091 | 1131 | 1 | 1111 | 1101 | 1121 | 1 |
| V8 | 2375 | 2332 | 2371 | 1 | 2351 | 2341 | 2361 | 1 |
| V9 | 2437 | 2393 | 2432 | 2 | 2412 | 2402 | 2422 | 1 |
| V10 | 2513 | 2468 | 2507 | 1 | 2488 | 2478 | 2498 | 1 |
| V11 | 2589 | 2544 | 2583 | 2 | 2563 | 2553 | 2573 | 1 |
| V12 | 3450 | 3396 | 3435 | 1 | 3416 | 3406 | 3426 | 1 |
| V13 | 3476 | 3421 | 3461 | 2 | 3441 | 3431 | 3451 | 2 |
| V14 | 3610 | 3554 | 3593 | 1 | 3574 | 3564 | 3584 | 1 |
| V15 | 3705 | 3649 | 3688 | 1 | 3668 | 3658 | 3678 | 1 |
| V16 | 3835 | 3777 | 3817 | 1 | 3797 | 3787 | 3807 | 1 |
| V17 | 3900 | 3841 | 3881 | 1 | 3861 | 3851 | 3871 | 1 |
| V18 | 4100 | 4039 | 4078 | 2 | 4,059 | 4049 | 4069 | 2 |
| V19 | 4108 | 4048 | 4087 | 2 | 4067 | 4057 | 4077 | 1 |
| V20 | 4244 | 4182 | 4221 | 2 | 4201 | 4191 | 4211 | 2 |
| VS1 | — | — | — | — | 674 | 664 | 684 | 1 |
| VS2 | — | — | — | — | 2901 | 2891 | 2911 | 1 |

In the case of sample A assessed according to example 1, the secondary detection array detected two more defects, which were not detected by the primary defection array. Critical defects detected by the primary detection array and the secondary detection array were paired and the second detection array improved the accuracy of their position. In comparison to the assessment according to example 0, the degree of accuracy was significantly increased and both adjacent rolls 8 had to be discarded only in two instances compared to the assessment according to example 0, where it was necessary to discard adjacent rolls 8 seven times.

Example 2—Positioning

On a spunbond-type nonwoven textile made from polypropylene, the primary detection array scans the primary detection area A1 directly upstream the winding onto a jumbo roll 9. The secondary detection area B is directly upstream the location of the cut of the textile 7. The sheet of textile is cut into rolls with a width of 150 mm.

The distance $W_1$ and $W_2$ are set with a deviation of +−5 mm.

Figure 3:
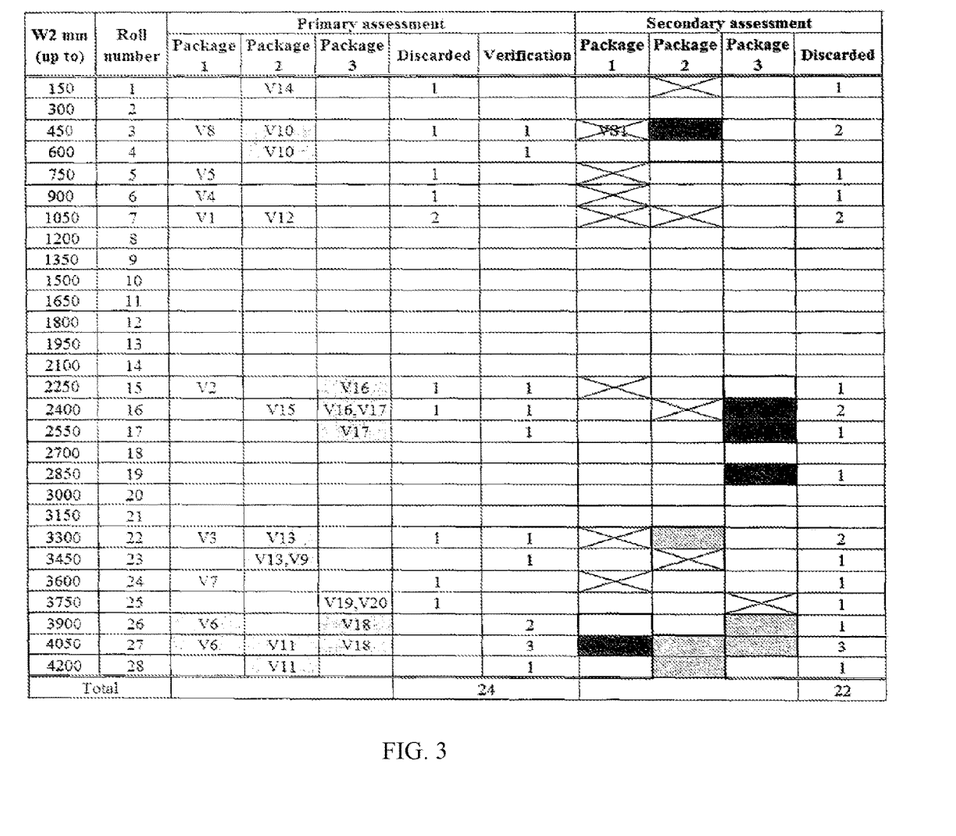
FIG. 3 is a table showing results of primary and secondary defect assessments of rolls of nonwoven textiles according to an exemplary embodiment of the present invention.

As shown in FIG. 3, the individual defects 13 detected in the primary detection area A1 are projected into a grid of the future cuts and the future rolls 8 are marked, where the defect 13 is safely in the middle of the roll (crossed-out) and the future rolls 8, where the defect 13 can be on both adjacent rolls (in the primary assessment coloured, in the secondary assessment framed in black). In the second assessment, the crossed out positions are no longer assessed and only not crossed out positions are assessed with special attention paid to coloured positions, where the location of the defect 13 is unclear.

During the secondary detection, two new critical defects (VS1 and VS2) were discovered, where one was already on a discarded roll (this defect was discovered by chance, it was no longer necessary to assess the field) and the second resulted in a second roll being discarded. At the same time, in 3 cases the position of unclear defects was clarified and only the rolls containing the defect were discarded. In three other cases, the defect was located too close to the cut and for safety reasons both adjacent rolls were discarded.

Compared to the primary assessment described in example 0, three additional safe rolls 8 were marked, which may be dispatched to the customer and one roll 8 contained a defect 13 (e.g. contamination), which must not be sent to the customer.

Example 3—Tertiary System

The procedure described in example 2 is supplemented with a tertiary detection array, which scans the tertiary detection area C, which is the winding of the package of small rolls 8. During the assessment of data from the tertiary detection array, a tear in package 2 was discovered on the blade between rolls 6 and 7. Both positions were on the basis of the assessment discarded.

INDUSTRIAL APPLICABILITY OF THE INVENTION

The invention is applicable for the detection of defects in fast moving fibrous material, namely regarding a fibrous material exhibiting compliance that causes changes to the dimensions of the textile sheet while it is travelling through the production line. Its use is advantageous during the production and treatment of nonwoven textiles. The main objective is to accurately identify the position of critical defects 13 while considering their location on the final roll 8 while at the same time ensuring both flexible production reaction and the detection of all defects that arise during the course of production. The main benefit is then limiting the amount of discarded material while concurrently ensuring that no critical defect reaches the customer.

The invention claimed is:

1. A method of detecting defects of a moving sheet of pliable fibrous material created by fibres falling onto a carrying belt, said method comprising the following steps:
   a. while a primary detection array is used to scan the moving sheet of fibrous material in at least one primary detection area, which the fibres, after falling onto the carrying belt, reach within a time shorter than 15 minutes, and information about identified defects is sent for assessment, where it forms a basis for assessing the need to adjust production parameters, and
   b. a secondary detection array scanning the sheet of fibrous material in at least one secondary detection area, which the fibres, after falling onto the carrying belt, reach later than the primary detection area, whereupon information about identified defects including the defects as identified by the primary detection array is sent to an assessment system, wherein, based on information about at least some defects identified by the primary detection array, areas of the sheet of fibrous material are determined for which an assessment of defects identified by the secondary detection array shall be performed, and this assessment is performed.

2. The method according to claim 1, wherein the information about identified defects includes coordinates determining position of a defect in the sheet of the assessed sheet of fibrous material.

3. The method according to claim 2, wherein the coordinates of the defects identified in step a. are recalculated before their use in step b. using a coefficient corresponding to change in width and length of the sheet of fibrous material during its transition from the primary detection area to the secondary detection area.

4. The method according to claim 2, wherein an expected measuring error in measurement of coordinates of defects is defined and that the coordinates of the defects identified by the primary detection array are compared in the assessment system with an information about expected cut lines in a subsequent cutting of the sheet of fibrous material into subsheets, whereupon defects are selected that are found to lie at a distance greater than the expected measuring error, at a distance larger than at least double the expected measuring error from the expected cut lines and the assessment of defects identified by the secondary detection array is performed only for areas corresponding to the expected subsheets not containing said selected defects.

5. The method according to claim 2, wherein an expected measuring accuracy of the measurement of coordinates of defects is defined and that the coordinates of the defects identified by the primary detection array are compared in the assessment system with the information about expected cut lines in a subsequent cutting of the sheet of fibrous material into sub sheets, and coordinates of defects that are found to lie on an expected cut line or at a distance smaller than or equal to double the expected measuring error are defined based on assessment of data gained by the secondary detection array.

6. The method according to claim 2, wherein an expected measurement error of defect coordinates is defined and that coordinates of defects identified by the primary detection array are compared within the assessment system with an information about expected cut lines in subsequent cutting of the sheet of fibrous material into sub sheets and the defects identified as lying on an expected cut line or at a distance smaller or equal to double the expected measurement error from an expected cut line are paired with the respective defects identified by the secondary detection array and these defects are assigned coordinates identified by the second detection array, and the assessment of the defects identified by the secondary detection array is performed only for areas corresponding to the expected subsheets containing neither defects the coordinates of which have been corrected by the process described above nor defects identified by the primary detection array as lying at a distance corresponding to at least double the expected measurement error.

7. The method according to claim 1, wherein a tertiary detection array scans the sheet of fibrous material in at least one tertiary detection area, which the sheet enters at or after cutting of the sheet of fibrous material into subsheets.

8. The method according to claim 1, wherein the performed assessments are combined for subsequent sorting of subsheets based on the identified defects contained in them.

* * * * *